United States Patent
Bayer et al.

(10) Patent No.: US 10,589,489 B2
(45) Date of Patent: Mar. 17, 2020

(54) COMPOSITE MATERIAL

(71) Applicant: Ecovative Design LLC, Green Island, NY (US)

(72) Inventors: Eben Bayer, Troy, NY (US); Gavin R. McIntyre, Troy, NY (US)

(73) Assignee: ECOVATIVE DESIGN LLC, Green Island, NY (US)

( * ) Notice: Subject to any disclaimer, the term of this patent is extended or adjusted under 35 U.S.C. 154(b) by 304 days.

(21) Appl. No.: 15/266,760

(22) Filed: Sep. 15, 2016

(65) Prior Publication Data
US 2017/0000040 A1    Jan. 5, 2017

Related U.S. Application Data

(62) Division of application No. 12/001,556, filed on Dec. 12, 2007, now Pat. No. 9,485,917.

(51) Int. Cl.

| | |
|---|---|
| *B32B 5/16* | (2006.01) |
| *A01G 18/00* | (2018.01) |
| *A01G 18/64* | (2018.01) |
| *C12N 1/14* | (2006.01) |
| *B32B 5/02* | (2006.01) |
| *C05D 9/00* | (2006.01) |
| *C12N 11/14* | (2006.01) |

(52) U.S. Cl.
CPC ............... *B32B 5/16* (2013.01); *A01G 18/00* (2018.02); *A01G 18/64* (2018.02); *B32B 5/02* (2013.01); *C05D 9/00* (2013.01); *C12N 1/14* (2013.01); *C12N 11/14* (2013.01); *B32B 2439/00* (2013.01); *Y10T 428/1348* (2015.01); *Y10T 428/249921* (2015.04); *Y10T 428/31504* (2015.04)

(58) Field of Classification Search
CPC ......... B32B 5/16; B32B 5/02; B32B 2439/00; A01G 18/00; C12N 1/14; Y10T 428/31504; Y10T 428/249921; Y10T 428/1348

See application file for complete search history.

(56) References Cited

U.S. PATENT DOCUMENTS 7,073,306 B1 *  7/2006  Hagaman .................. E04B 1/35
                                                     249/20

OTHER PUBLICATIONS

P. Stamets "Mycelium Running", 2005, Ten Speed Press, 356 pages, pp. 18, 56, 58, 59, 85, 149, 157, 160, and 291 Only.*
Sawdust, universaloilfield.org, downloaded on Aug. 23, 2018, 4 pages.*
"Fungal Biotechnology in Agricultural, Food, and Environmental Applications", Editor: Dilip K. Arora, Publisher Marcel Dekker, Inc., 2004, Chapter 21, "Production of Edible Fungi", by R. D. Rai, p. 383-404.*
Mushroom Growers' Handbook 2 (Shiitake Cultivation, Part I Shiitake, 2005, Published by Mush World, p. 73-90.*
Definition of composite, dictionary downladed on Nov. 21, 2018, 1 page.*
Wood defined by Wikipedia downladed on Nov. 26, 2018, 1 page.*
Ross, P. Pure Culture 1997-Present 10 pages, http://billhoss.phwebhosting.com/ross/index.php?kind.

* cited by examiner

*Primary Examiner* — Kade Ariani
(74) *Attorney, Agent, or Firm* — Francis C. Hand; Carella, Byrne, et al

(57) ABSTRACT

The composite material is comprised of a substrate of discrete particles and a network of interconnected mycelia cells bonding the discrete particles together. The composite material is made by inoculating a substrate of discrete particles and a nutrient material with a preselected fungus. The fungus digests the nutrient material over a period of time sufficient to grow hyphae and to allow the hyphae to form a network of interconnected mycelia cells through and around the discrete particles thereby bonding the discrete particles together to form a self-supporting composite material.

18 Claims, 13 Drawing Sheets

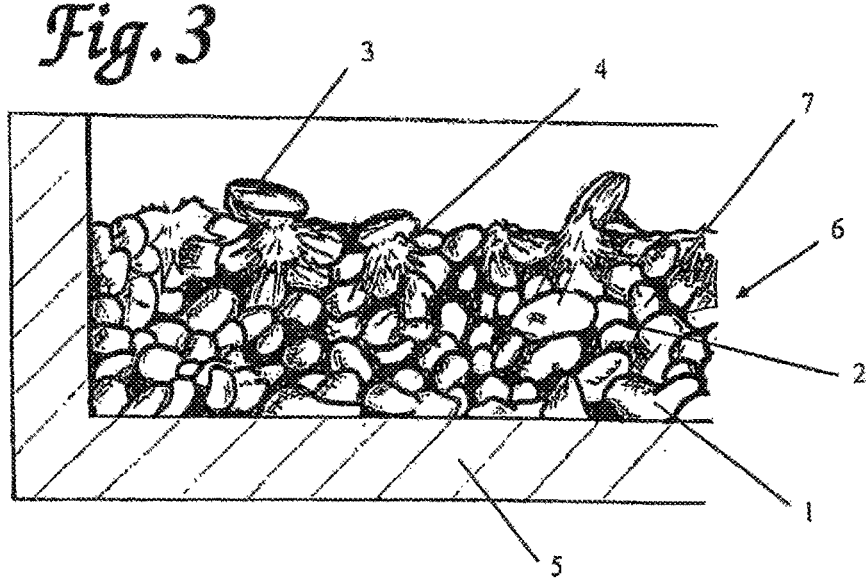
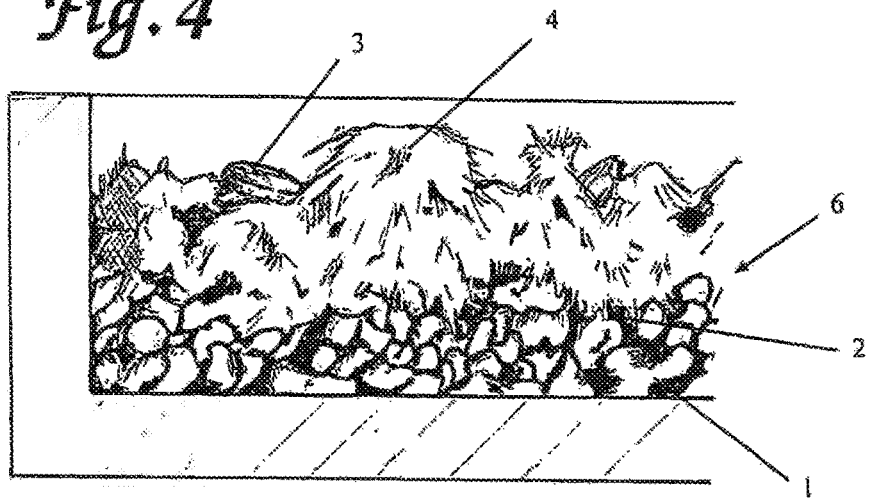
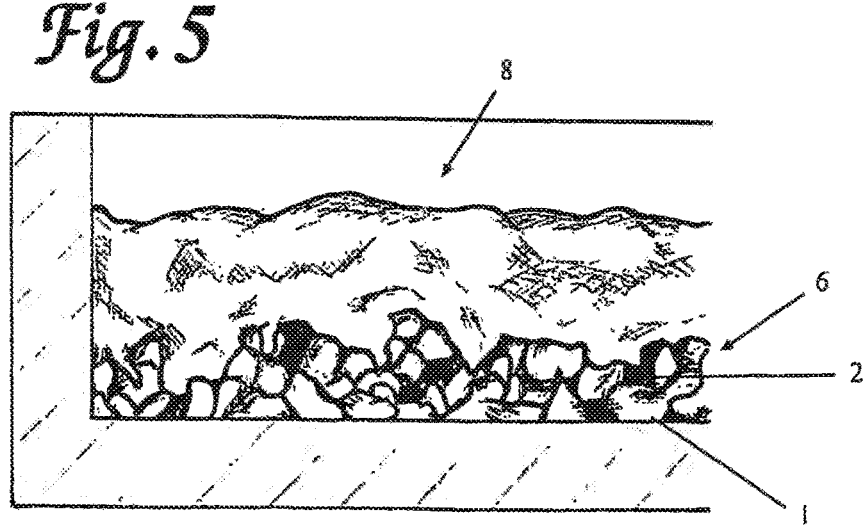

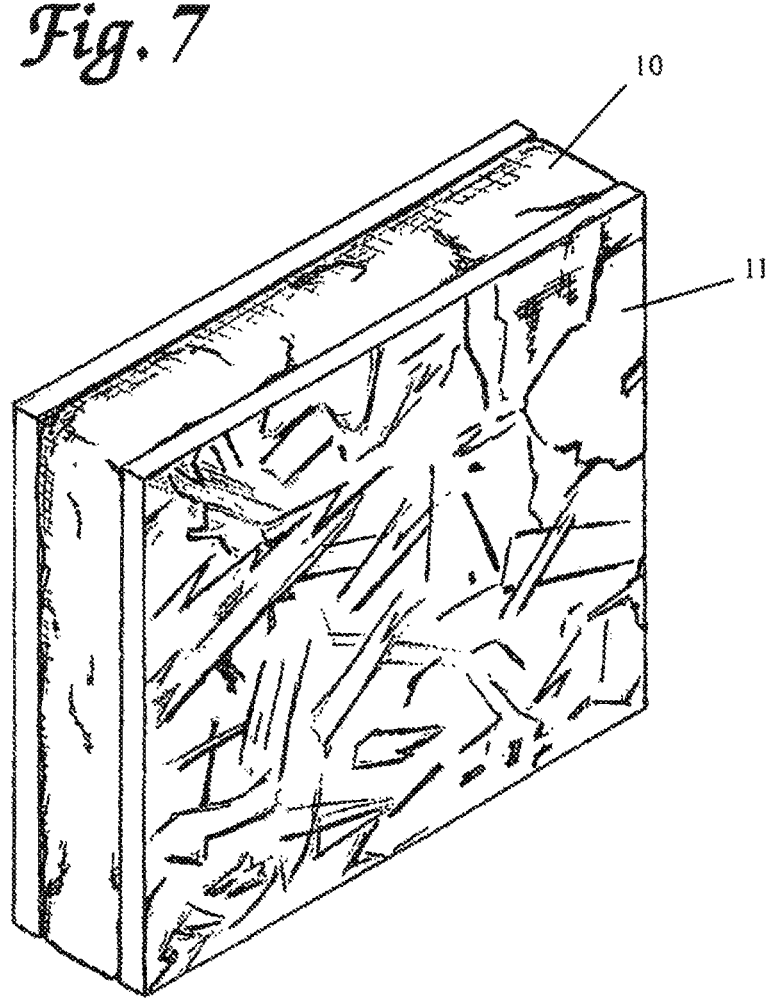

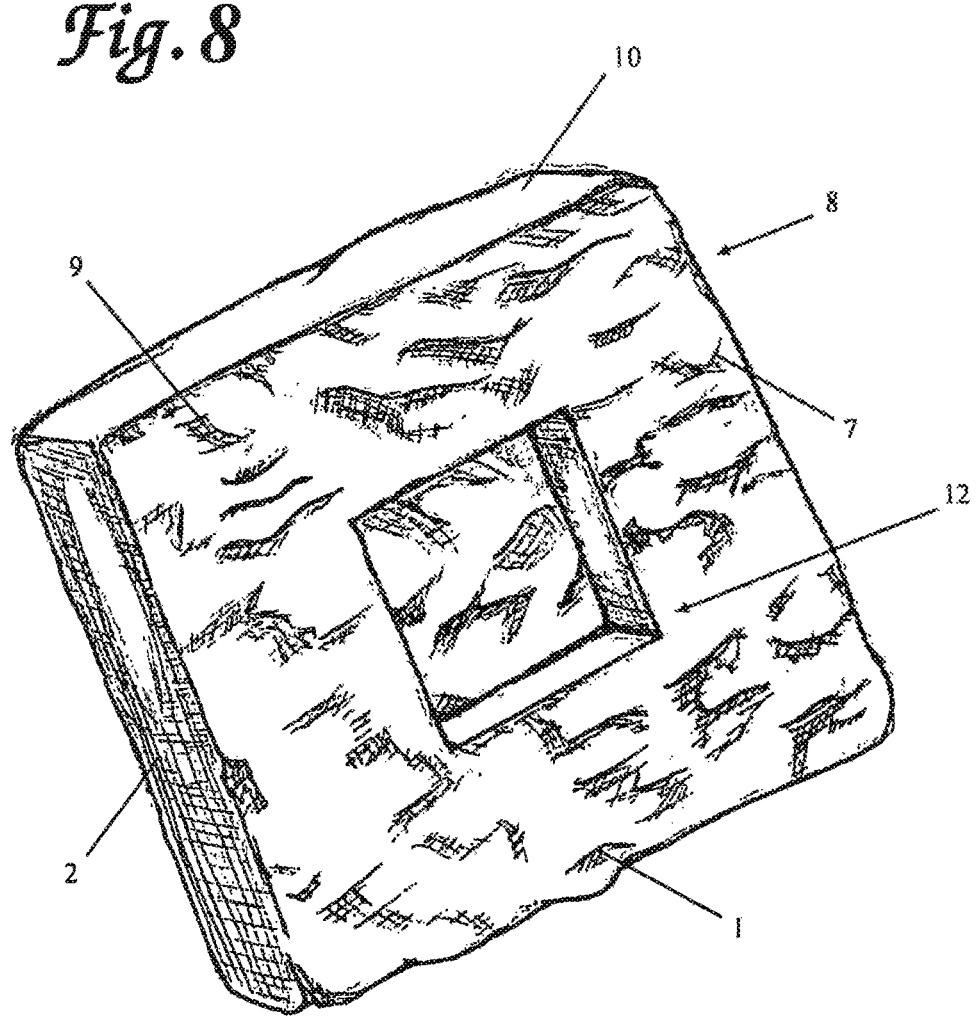

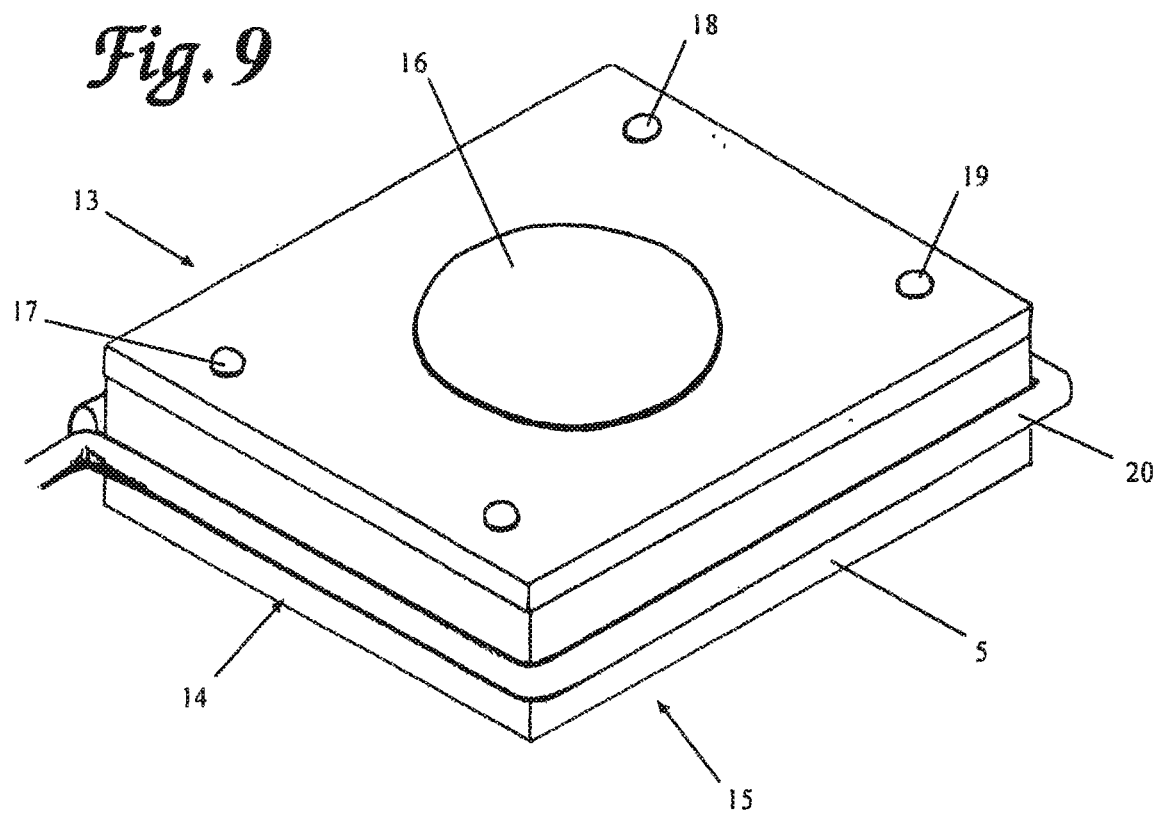
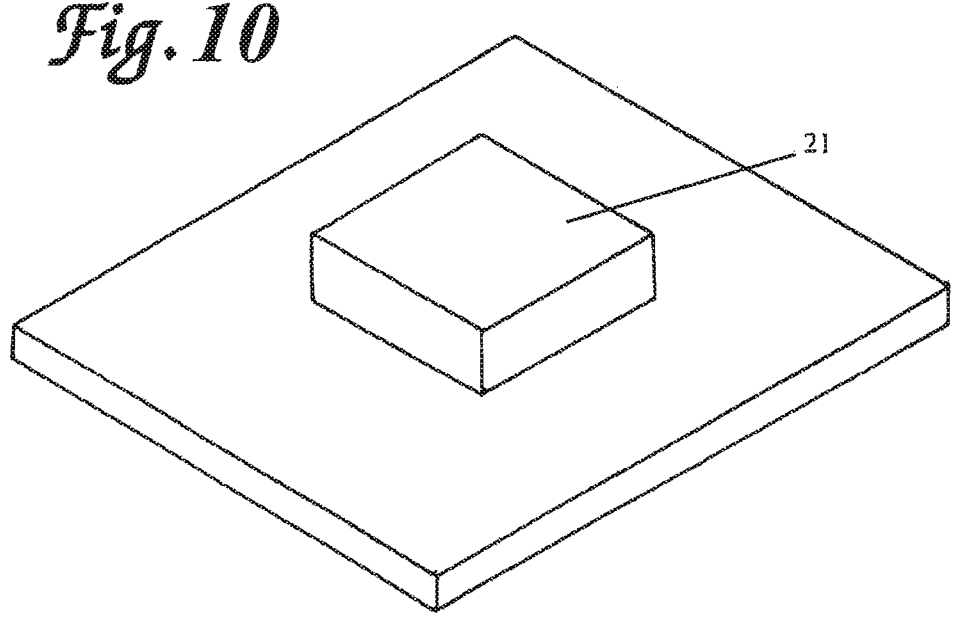

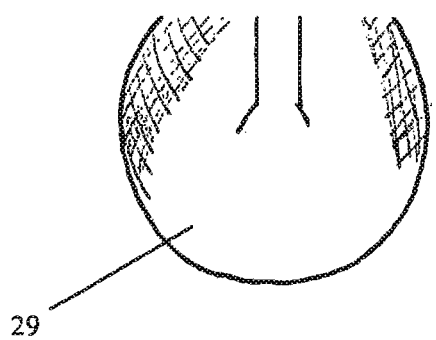
Fig. 17
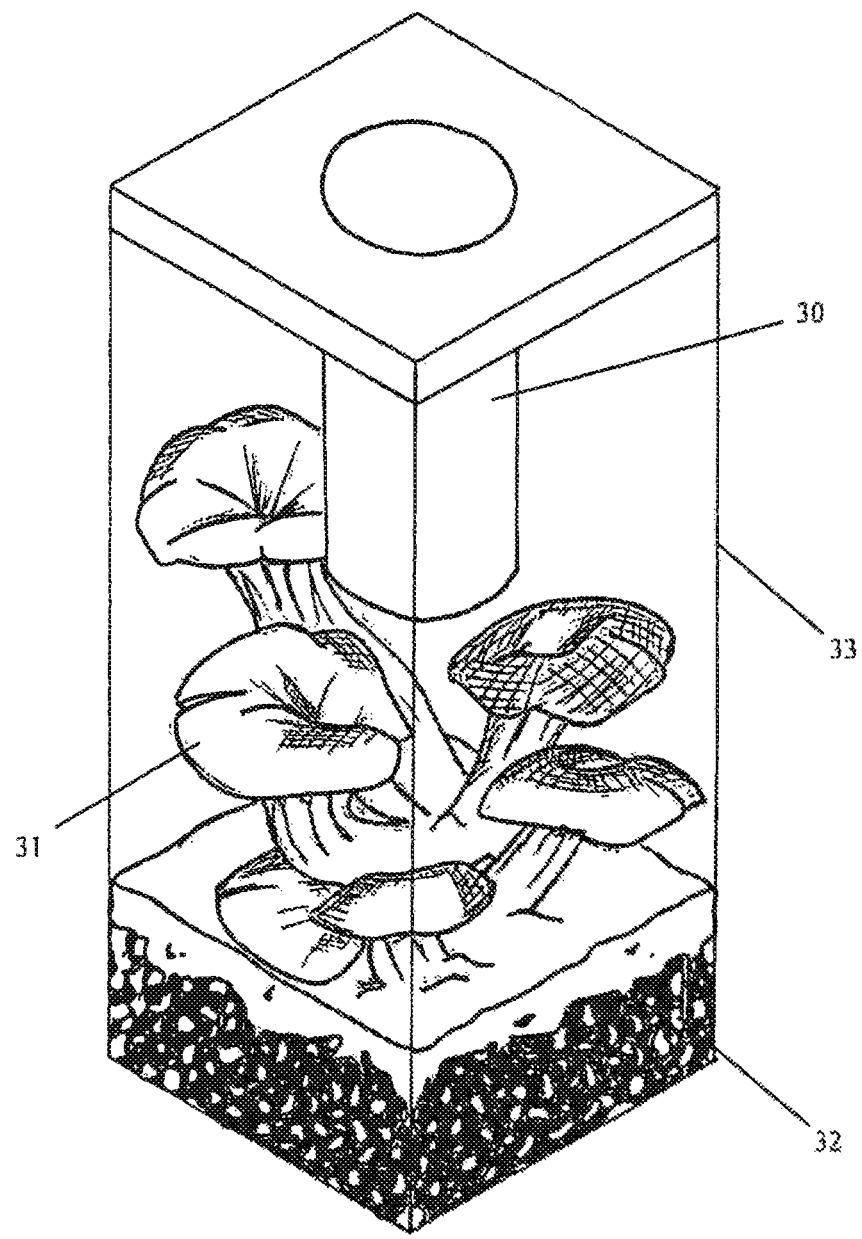

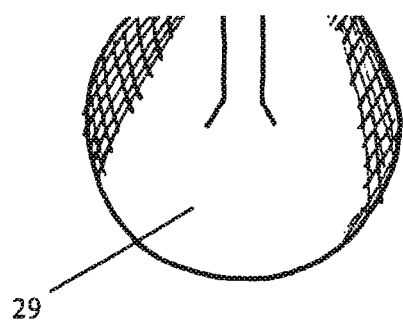
Fig. 18
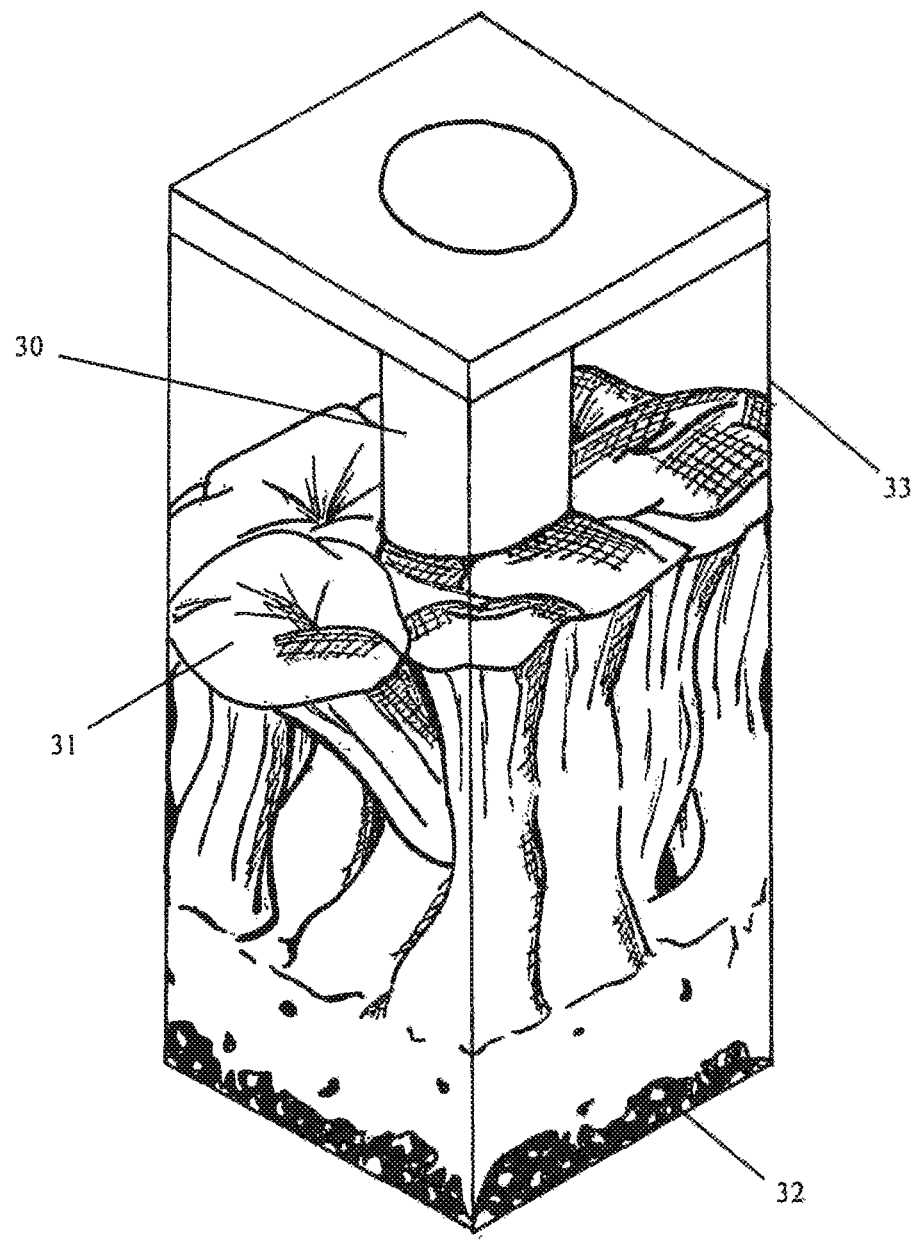

US 10,589,489 B2

COMPOSITE MATERIAL

This invention claims the benefit of Provisional Patent Application No. 60/875,243 filed Dec. 15, 2006 and Provisional Patent Application No. 60/927,458 filed May 3, 2007, the contents of each being incorporated by reference herein and is a Division of U.S. Ser. No. 12/001,556, filed Dec. 12, 2007.

This invention relates to a composite material. More particularly, this invention relates to a composite material grown from organic material. Still more particularly, this invention relates to composite materials for use as organic insulation and organic packaging.

BACKGROUND OF THE INVENTION

Materials are produced today using a range of processes ranging from time intensive outdoor growth and harvesting to energy intensive factory centric production.

As demand for raw goods and materials rise, the associated cost of such materials rises. This places greater pressure on limited raw materials, such as minerals, ores, and fossil fuels, as well as on typical grown materials, such as trees, plants, and animals. Additionally, the production of many materials and composites produces significant environmental downsides in the form of pollution, energy consumption, and a long post use lifespan.

Conventional materials such as expanded petroleum based foams are not biodegradable and require significant energy inputs to produce in the form of manufacturing equipment, heat and raw energy.

Conventionally grown materials, such as trees, crops, and fibrous plants, require sunlight, fertilizers and large tracts of farmable land.

Finally, all of these production processes have associated waste streams, whether they are agriculturally or synthetically based.

Fungi are some of the fastest growing organisms known. They exhibit excellent bioefficiency, of up to 80%, and are adept at converting raw inputs into a range of components and compositions. Fungi are composed primarily of a cell wall that is constantly being extended at the tips of the hyphae. Unlike the cell wall of a plant, which is composed primarily of cellulose, or the structural component of an animal cell, which relies on collagen, the structural oligosaccharides of the cell wall of fungi rely primarily on chitin. Chitin is strong, hard substance, also found in the exoskeletons of arthropods. Chitin is already used within multiple industries as a purified substance. These uses include: water purification, food additives for stabilization, binders in fabrics and adhesives, surgical thread, and medicinal applications.

Given the rapid growth times of fungi, its hard and strong cellular wall, its high level of bioefficiency, its ability to utilize multiple nutrient and resource sources, and, in the filamentous types, its rapid extension and exploration of a substrate, materials and composites, produced through the growth of fungi, can be made more efficiently, cost effectively, and faster, than through other growth processes and can also be made more efficiently and cost effectively then many synthetic processes.

Numerous patents and scientific procedure exists for the culturing of fungi for food production, and a few patents detail production methods for fungi with the intent of using its cellular structure for something other than food production. For instance U.S. Pat. No. 5,854,056 discloses a process for the production of "fungal pulp", a raw material that can be used in the production of paper products and textiles.

Accordingly, it is an object of the invention to provide a composite material made by the culturing of filamentous and composed in part, or entirely of, hyphae and its aggregative form, mycelia and mycelium.

It is another object of the invention to provide a composite structure made in part of cultured fungi.

It is another object of the invention to provide a mixture of particles for use in the growing of filamentous fungi to produce a composite material.

Basically, the invention provides a self-supporting composite material comprised of a substrate of discrete particles and a network of interconnected mycelia cells extending through and around the discrete particles and bonding the discrete particles together.

In order to produce the composite material a fungi is cultured for the production of the material using the vegetative phase of the fungi.

This method uses the growth of hyphae, collectively referred to as mycelia or mycelium, to create materials composed of the fungi cellular tissue. This method expressly includes the growth of hyphae to create composites, utilizing particles, fibers, meshes, rods, elements, and other bulking agents, as a internal component of the composite, where the hyphae and other cellular tissue and extra cellular compounds act as a bonding agent and structural component.

In one embodiment, the method of making a composite material comprises the steps of forming an inoculum including a preselected fungus; forming a mixture of a substrate of discrete particles and a nutrient material that is capable of being digested by the fungi; adding the inoculum to the mixture; and allowing the fungus to digest the nutrient material in the mixture over a period of time sufficient to grow hyphae and to allow the hyphae to form a network of interconnected mycelia cells through and around the discrete particles thereby bonding the discrete particles together to form a self-supporting composite material.

Where at least one of the Inoculum and the mixture includes water, the formed self-supporting composite material is heated to a temperature sufficient to kill the fungus or otherwise dried to remove any residual water to prevent the further growth of hyphae.

The method may be carried out in a batchwise manner by placing the mixture and inoculum in a form so that the finished composite material takes on the shape of the form. Alternatively, the method may be performed in a continuous manner to form an endless length of composite material.

The method employs a step for growing filamentous fungi from any of the divisions of phylum Fungi. The examples that are disclosed focus on composites created from basidiomycetes, e.g., the "mushroom fungi" and most ecto-mycorrhizal fungi. But the same processes will work with any fungi that utilizes filamentous body structure. For example, both the lower fungi, saprophytic oomycetes, the higher fungi, divided into zygomycetes and endo-mycorrhizal fungi as well as the ascomycetes and deuteromycetes are all examples of fungi that posses a filamentous stage in their life-cycle. This filamentous stage is what allows the fungi to extend through its environment creating cellular tissue that can be used to add structural strength to a loose conglomeration of particles, fibers, or elements.

The invention also provides materials and composite materials, whose final shape is influenced by the enclosure, or series of enclosures, that the growth occurs within and/or around.

In accordance with the invention, the discrete particles may be of any type suited to the use for which the material is intended. For example, the particles may be selected from the group consisting of at least one of vermiculite and perlite where the composite material is to be used as a fire-resistant wall. Also, the particles may be selected from the group consisting of at least one of straw, hay, hemp, wool, cotton, rice hulls and recycled sawdust where composite material is to be used for insulation and strength is not a necessary criteria. The particles may also include synthetic insulating particles, such as, foam based products and polymers.

These and other objects and advantages will become more apparent from the following detailed description taken in conjunction with the accompanying drawings wherein:

FIG. 3 illustrates an inoculated substrate before growth in an enclosure in accordance with the invention;

FIG. 4 illustrates an inoculated substrate after three days of growth in accordance with the invention;

FIG. 5 illustrates an inoculated substrate nearing the end of the growth in accordance with the invention;

FIG. 7 illustrates a composite with internal features in accordance with the invention.

FIG. 8 illustrates an enclosure containing a filter disk, temperature sensor, humidity sensor and heat exchange mechanism in accordance with the invention;

FIG. 9 illustrates an enclosure lid with a rectangular extrusion in accordance with the invention;

FIG. 10 illustrates a layered substrate layer in accordance with the invention;

Figure 1:
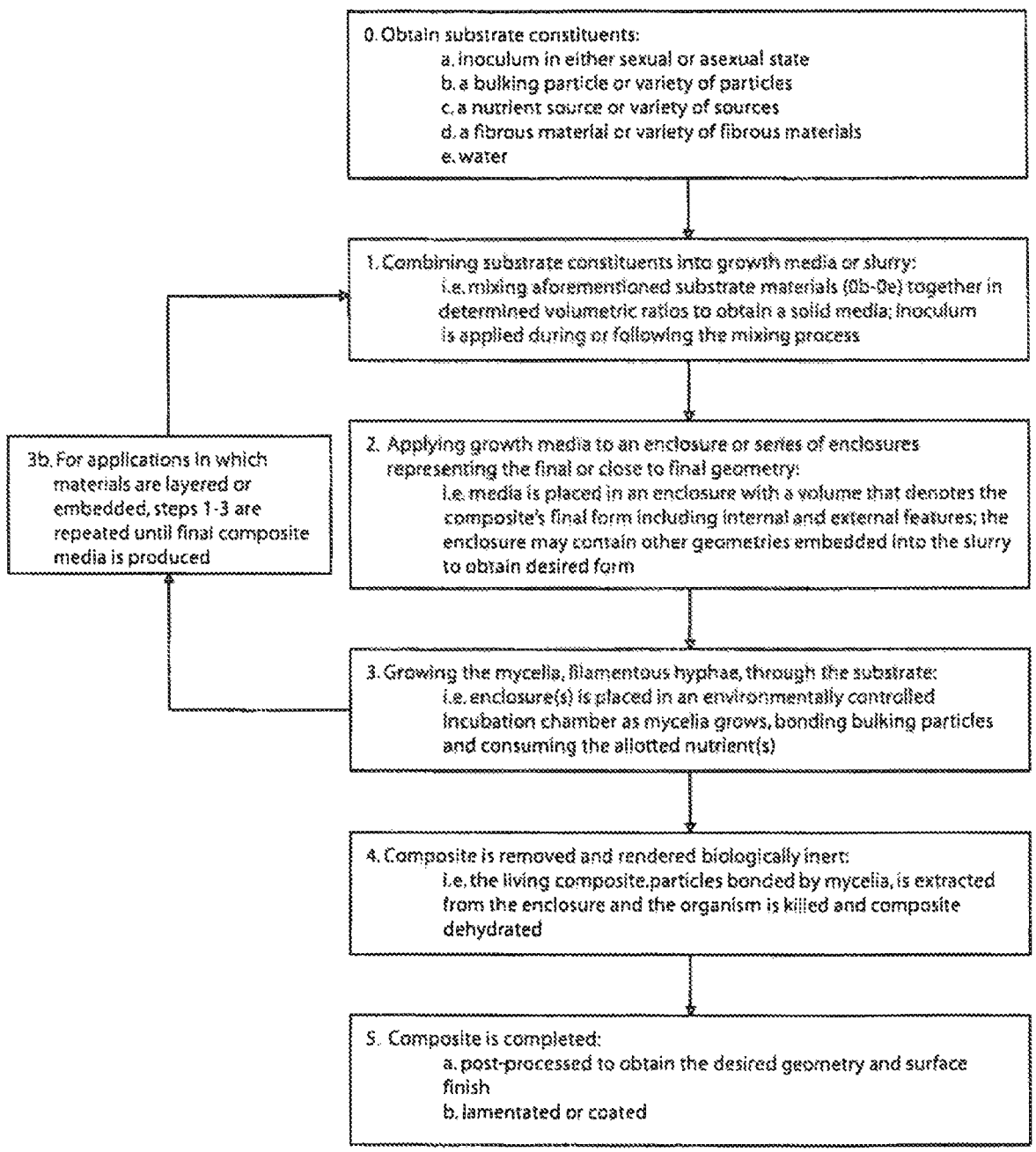
FIG. 1 illustrates a simplified flow chart of the method employed for making a fungi bonded material in accordance with the invention.

Referring to FIG. 1, the method of making a self-supporting structural material is comprised of the following steps.

0. Obtain substrate constituents, i.e. inoculum in either a sexual or asexual state, a bulking particle or a variety of bulking particles, a nutrient source or a variety of nutrient sources, a fibrous material or a variety of fibrous materials and water.
1. combining the substrate constituents into a growth media or slurry by mixing the substrate materials together in volumetric ratios to obtain a solid media while the inoculum is applied during or following the mixing process.
2. applying the growth media to an enclosure or series of enclosures representing the final or close to final geometry. The media is placed in an enclosure with a volume that denotes the composite's final form including internal and external features. The enclosure may contain other geometries embedded in the slurry to obtain a desired form.
3. growing the mycelia, i.e. filamentous hyphae, through the substrate. The enclosure is placed in an environmentally controlled incubation chamber as mycelia grows bonding the bulking particles and consuming the allotted nutrient(s).

3a. repeating steps 1-3 for applications in which materials are layered or embedded until the final composite media is produced.

4. removing the composite and rendering the composite biologically inert. The living composite, i.e. the particles bonded by the mycelia, is extracted from the enclosure and the organism is killed and the composite dehydrated.
5. completing the composite. The composite is post-processed to obtain the desired geometry and surface finish and laminated or coated.

The inoculum is produced using any one of the many methods known for the cultivation and production of fungi including, but not limited to, liquid suspended fragmented mycelia, liquid suspended spores and mycelia growing on solid or liquid nutrient.

Inoculum is combined with the engineered substrate, which may be comprised of nutritional and non-nutritional particles, fibers, or other elements. This mixture of inoculum and substrate is then placed in an enclosure.

In step 3, hyphae are grown through the substrate, with the net shape of the substrate bounded by the physical dimensions of the enclosure. This enclosure can take on any range of shapes including rectangles, boxes, spheres, and any other combinations of surfaces that produce a volume. Growth can occur both inside the enclosure and outside of the enclosure depending on desired end shape. Similarly, multiple enclosures can be combined and nested to produce voids in the final substrate.

Other elements embedded with the slurry may also become integrated into the final composite through the growth of the hyphae.

The hyphae digest the nutrients and form a network of interconnected mycelia cells growing through and around the nutrients and through and around the non-nutrient particles, fibers, or elements. This growth provides structure to the once loose particles, fibers, elements, and nutrients, effectively bonding them in place while bonding the hyphae to each other as well.

In step 4, the substrate, now held tightly together by the mycelia network, is separated from the enclosure, and any internal enclosures or elements are separated away, as desired.

The above method may be performed with a filamentous fungus selected from the group consisting of ascomycetes, basidiomycetes, deuteromycetes, oomycetes, and zygomycetes. The method is preferably performed with fungi selected from the class: Holobasidiomycete.

The method is more preferably performed with a fungus selected from the group consisting of:

*pleurotus ostreatus*
*Agrocybe brasiliensis*
*Flammulina velutipes*
*Hypholoma capnoides*
*Hypholoma sublaterium*
*Morchella angusticeps*
*Macrolepiota procera*
*Coprinus comatus*
*Agaricus arvensis*
*Ganoderma tsugae*
*Inonotus obliquus*

The method allows for the production of materials that may, in various embodiments, be characterized as structural, acoustical, insulating, shock absorbing, fire protecting, biodegrading, flexible, rigid, water absorbing, and water resisting and which may have other properties in varying degrees based on the selection of fungi and the nutrients. By varying the nutrient size, shape, and type, the bonded bulking particle, object, or fiber, size, shape, and type, the environmental conditions, and the fungi strain, a diverse range of material types, characteristics and appearances can be produced using the method described above.

The present invention uses the vegetative growth cycle of filamentous fungi for the production of materials comprised entirely, or partially of the cellular body of said fungi collectively known as mycelia.

Figure 2:
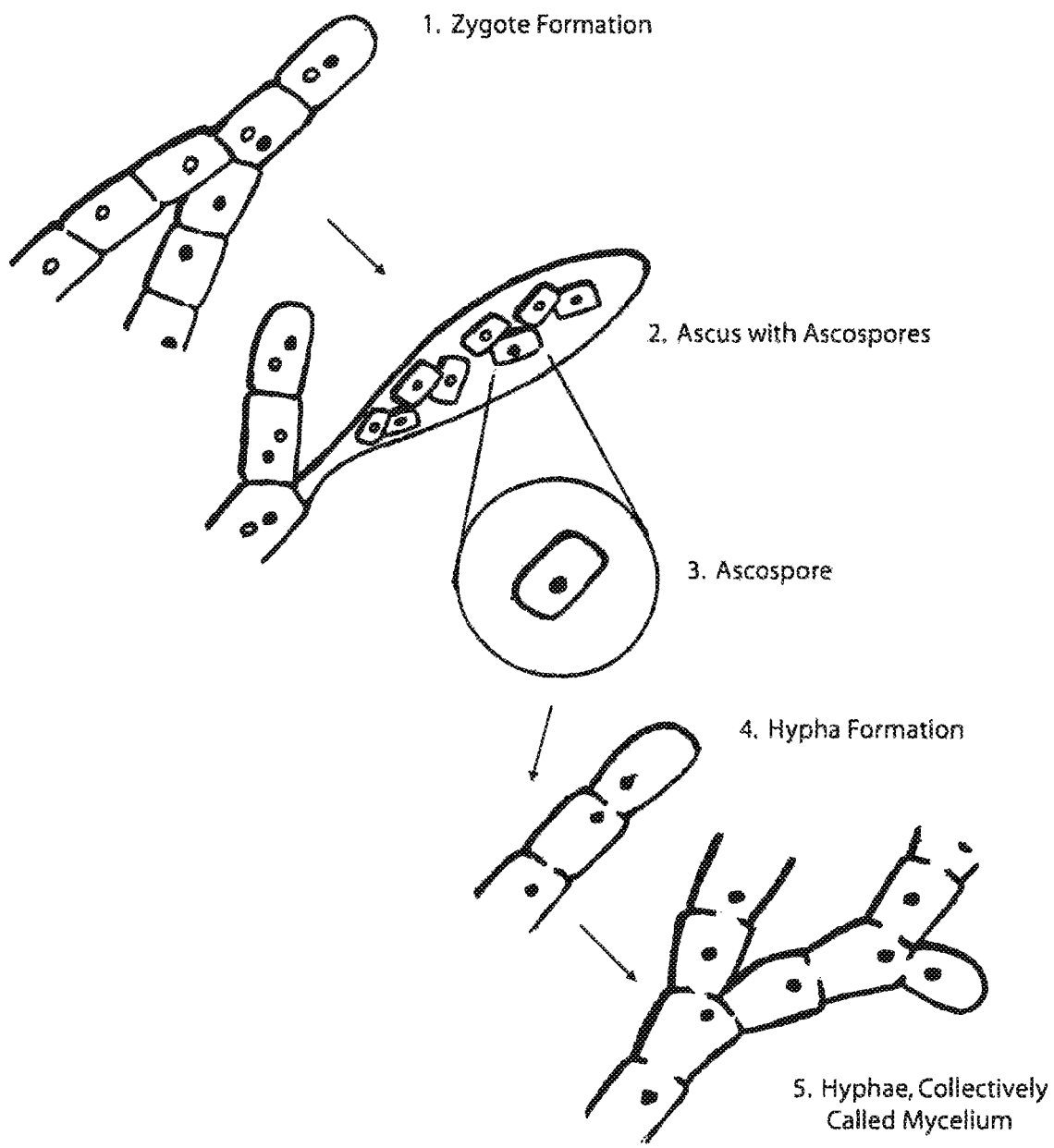
FIG. 2 illustrates a schematic life cycle of *Pleurotus ostreatus;*

FIG. 2 shows a schematic representation of the life cycle of *Pleurotus Ostreatus*, filamentous fungi. The area of interest for this invention is the vegetative state of a fungi's life cycle where a fungi is actively growing through the extension of its tube like hyphae.

In this Description, the following definitions are specifically used:

Spore: The haploid, asexual bud or sexual reproducing unit, or "seed", of a fungus.

Hyphae: The thread-like, cellular tube of filamentous fungi which emerge and grow from the germination of a fungal spore.

Mycelium: The collection of hyphae tubes originating from a single spore and branching out into the environment.

Inoculum: Any carrier, solid, aerated, or liquid, of a organism, which can be used to transfer said organism to another media, medium, or substrate.

Nutrient: Any complex carbohydrate, polysaccharide chain, or fatty group, that a filamentous fungi can utilize as an energy source for growth.

Fruiting Body: A multicellular structure comprised of fungi hyphae that is formed for the purpose of spore production, generally referred to as a mushroom.

Fungi Culturing for Material Production

Methodology

Procedures for Culturing Filamentous Fungi for Material Production.

All methods disclosed for the production of grown materials require an inoculation stage wherein an inoculum is used to transport a organism into a engineered substrate. The inoculum, carrying a desired fungi strain, is produced in sufficient quantities to inoculate the volume of the engineered substrates; inoculation volume may range from as low as 1% of the substrates total volume to as high as 80% of the substrates volume. Inoculum may take the form of a liquid carrier, solid carrier, or any other known method for transporting a organism from one growth supporting environment to another.

Generally, the inoculum is comprised of water, carbohydrates, sugars, vitamins, other nutrients and the fungi. Depending on temperature, initial tissue amounts, humidity, inoculum constituent concentrations, and growth periods, culturing methodology could vary widely.

EXAMPLE 1

Production of a Grown Material Using an Enclosure

*Plearotus Ostreatus*, or any other filamentous fungi, is cultured from an existing tissue line to produce a suitable mass of inoculum. The inoculum may take the form of a solid carrier, liquid carrier, or any other variation there of.

To produce a grown material using an enclosure based manufacturing technique, the following steps are taken:

1. Creation of an engineered substrate comprised of nutritional particles, fibers, non-nutritional particles, and other elements.
2. Disposition of the substrate within an enclosure or series of enclosures with voids designed to produce the desired final shape.
3. Inoculation of the substrate within the enclosure with the inoculum containing the desired fungi strain.
4. Growing the desired fungi strain through the engineered substrate within the enclosure or enclosures.
5. Removal of the substrate from the enclosure or enclosures.

Alternatively, the method may use the following steps:
1. Creation of an engineered substrate comprised of nutritional particles, fibers, non-nutritional particles, and other elements.
2. Inoculation of the engineered substrate with the inoculum containing the desired fungi strain.
3. Disposition of the substrate within an enclosure or series of enclosures with voids designed to produce the desired final shape.
4. Growing the desired fungi strain through the engineered substrate within the enclosure or enclosures.
5. Removal of the bonded engineered substrate from the enclosure or enclosures.

Alternatively, the method may use the following steps:
1. Creation of an engineered substrate comprised of nutritional particles, fibers, non-nutritional particles, and other elements.
2. Inoculation of the engineered substrate with the inoculum containing the desired fungi strain.
   (Growing of fungi through the engineered substrate in an enclosure such that the entire engineered substrate could be considered an inoculum. The substrate may be partially agitated during this time, or broken up before proceeding to step 3.)
3. Disposition of the engineered substrate inoculum within an enclosure or series of enclosures with voids designed to produce the desired final shape.
4. Growing the desired fungi strain through the engineered substrate within the enclosure or enclosures.
5. Removal of the bonded engineered substrate from the enclosure or enclosures.

As in other disclosed embodiments, the bonding of the grown material is derived primarily from the fungi cellular body, mycelia, that forms throughout and around the engineered substrate. The overall properties of the material are set by the behavior of multiple particles, fibers, and other elements, acting in concert to impart material characteristics, much like in the creation of other composites. The enclosure or enclosures sets the final shape that of the material.

Referring to FIG. 2, the life cycle of *Pleurotus ostreatus* proceeds from zygote formation (1) to ascus (2) with multiplicity of ascopores (3) and then to hypha formation (4) with the hyphae being collectively called mycelium (5).

Grown Material within an Enclosure

First Embodiment—FIGS. 3-6

FIG. 3 shows a side view of one embodiment i.e. an insulating composite, just after inoculation has taken place.

In this embodiment, a group of nutritional particles 1 and a group of insulating particles 2 were placed in an enclosure 5 to form an engineered substrate 6 therein. The enclosure 5 has an open top and determines the final net shape of the grown composite. Thereafter, an inoculum 3 was applied directly to the surface of the engineered substrate 6.

Shortly after the inoculum 3 was applied to the surface, hyphae 4 were visible extending away from the inoculum 3 and into and around the nutritional particles 1 and insulating particles 2.

FIG. 4 shows a side view of the same embodiment described above, i.e. an insulating composite, approximately 3 days after the inoculum 3 was applied to the surface of the engineered substrate 6. Hyphae 3 have now penetrated into the engineered substrate 6 and are beginning to bond insulating particles 2 and nutritional particles 1 into a coherent whole.

FIG. 5. shows a side view of the same embodiment of FIGS. 3 and 4, i.e. an insulating composite, approximately 7 days after the inoculum 3 was applied to the surface of the engineered substrate 6. Hyphae 3, collectively referred to as mycelia 7, have now fully colonized the top half of engineered substrate 6, bonding insulating particles 2 and nutritional particles 1 into a coherent whole.

Figure 6:
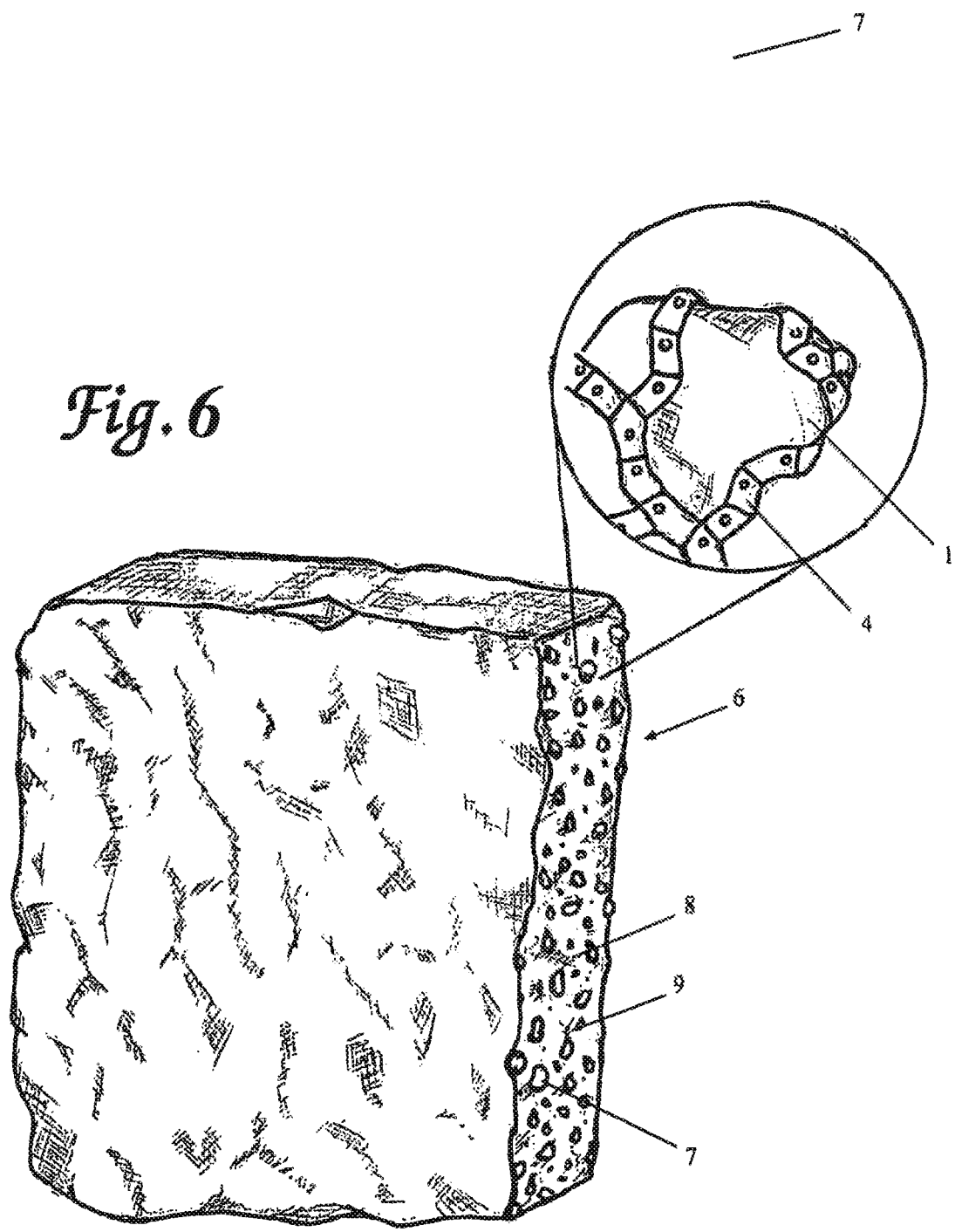
FIG. 6 illustrates a final composite of one embodiment composed of nutrient particles and a bulking particle in accordance with the invention.

FIG. 6 shows a side view of the same embodiments of FIGS. 3, 4 and 5, i.e. an insulating composite, after the engineered substrate 6 has been fully colonized and all of the discrete particles bonded by mycelia 7. A cutaway view shows a detail of a single insulating particle bound by a number of hyphae 4. Also shown within this embodiment are fibers 9 bound within mycelia 8.

EXAMPLE 2

Layered Molding

To produce a grown material using a "layered enclosure based" manufacturing technique, the following steps are taken:
1. Creation of an engineered substrate composed partially or entirely of nutritional particles, fibers, and other elements, and composed partially or entirely of non-nutritional particles, fibers, and other elements.
2. Disposition of a fraction of the engineered substrate to an enclosure or series of enclosures with voids designed to produce the desired final shape.
3. Inoculation of the substrate within the enclosure with the inoculum containing the desired fungi strain or type. Inoculation can also occur during the substrate creation stage, prior to moving the substrate into the enclosure or series of enclosures.
4. Growing the desired fungi strain through the engineered substrate within the enclosure or enclosures.
5. Adding, as desired, additional layers of the engineered substrate or additional layers of an engineered substrate with a differing composition.
6. Growing the desired fungi strain through the additional layer of the engineered substrate.
7. Repeating, as necessary, to develop desired feature height, material size, and material composition.
8. Removal of the bonded engineered substrate from the enclosure or enclosures.

Alternatively, the method may use the following steps:
1. Creation of an engineered substrate composed partially or entirely of nutritional particles, fibers, and other elements, and composed partially or entirely of non-nutritional particles, fibers, and other elements.
2. Inoculation of the engineered substrate within the enclosure with the inoculum containing the desired fungi strain or type.
3. Disposition of a fraction of the engineered substrate to an enclosure or series of enclosures with voids designed to produce the desired final shape.
4. Growing the desired fungi strain through the engineered substrate within the enclosure or enclosures.
5. Adding, as desired, additional layers of the engineered substrate or additional layers of an engineered substrate with a differing composition.
6. Growing the desired fungi strain through the additional layer of the engineered substrate.
7. Repeating, as necessary, to develop desired feature height, material size, and material composition.
8. Removal of the bonded engineered substrate from the enclosure or enclosures.

EXAMPLE 3

Continuous Production

To produce a grown material using a "continuous based" manufacturing technique the following steps are taken:
1. Creation of an engineered substrate composed partially or entirely of nutritional particles, fibers, and other elements, and composed partially or entirely of non-nutritional particles, fibers, and other elements.
2. Disposition of the substrate to an open-ended enclosure or series of enclosures with continuous voids designed to produce the desired final shape.
3. Inoculation of the substrate within the enclosure with the inoculum containing the desired fungi strain or type. Inoculation can also occur during the substrate creation stage, prior to moving the substrate into the enclosure or series of enclosures.
4. Growing the desired fungi strain through the engineered substrate within the enclosure or enclosures.
5. Moving the substrate through the open ended enclosure such that the initial inoculated substrate volume reaches the end of the enclosure as hyphae growth has reached maximum density
6. Moving the bonded engineered substrate out of the open-ended enclosure.

EXAMPLE 4

Static Embodiment—Composite

FIG. 6 shows a perspective view of one embodiment of a mycelia bonded composite composed of nutritional particles, bulking particles, fibers, and insulating particles. In this embodiment of a mycelia bonded composite, the following growth conditions and materials were used: The engineered substrate was composed of the following constituents in the following percentages by dry volume:
1. Rice Hulls, purchased from Rice World in Arkansas, 50% of the substrate.
2. Horticultural Perlite, purchased from World Mineral of Santa Barbara, Calif., 15% of the substrate.
3. DGS, dried distillers grains, sourced from Troy Grain Traders of Troy N.Y., 10% of the substrate.
4. Ground cellulose, composed of recycled paper ground into an average sheet size of 1 mm×1 mm, 10% of the substrate.
5. Coco coir, sourced from Mycosupply, 10% of the substrate.
6. Inoculum composed of rye grain and inoculated with *Plearotus Ostreatus*, 3% of the substrate.

7. Birch sawdust, fine ground, 2% of the substrate by volume.
8. Tap water, from the Troy Municipal Water supply, was added until the mixture reached field capacity, an additional 30% of the total dry substrate volume was added in the form of water.

These materials were combined together in a dry mix process using a rotary mixer to fully incorporate the particles, nutrients, and fibers. Water was added in the final mixing stage. Total mixing time was 5 minutes.

The enclosures were incubated for 14 days at 100% RH humidity and at a temperature of 75° Fahrenheit. The enclosures serve as individual microclimates for each growing substrate set. By controlling the rate of gas exchange, humidity can be varied between RH 100%, inside an enclosure, and the exterior humidity, typically RH 30-50%. Each rectangular enclosure fully contained the substrate and inoculum preventing gaseous exchange. Opening the enclosures lids after 5 and 10 days allowed gaseous exchange. In some cases, lids included filter disks allowing continuous gas exchange.

After 14 days of growth, the enclosures were removed from the incubator. The loose fill particles and fibers having been bonded into a cohesive whole by the fungi's mycelium produced a rectangular panel with dimensions closely matching those of the growth enclosure. This panel was then removed from the enclosure by removing the lid, inverting the growth enclosure, and pressing gently on the bottom.

The mycelia bonded panel was then transferred to a drying rack within a convection oven. Air was circulated around the panel until fully dry, about 4 hours. Air temperature was held at 130 degrees Fahrenheit.

After drying, the now completed composite is suitable for direct application within a wall, or can be post processed to include other features or additions including water resistant skins, stiff exterior panel faces, and paper facings.

Within the above embodiment, the ratios and percentages of bulking particles, insulating particles, fibers, nutrients, inoculum, and water can be varied to produce composites with a range of properties. The materials expanded perlite compositions can vary from 5%-95% of the composite by volume. Other particles, including exfoliated vermiculite, diatomic earth, and ground plastics, can be combined with the pertite or substituted entirely. Particle sizes, from horticultural grade pertite to filter grade perlite are all suitable for composite composition and many different composite types can be created by varying the ratio of perlite particle size or vermiculite or diatomic earth particle size.

Rice hulls can compose anywhere from 5-95% of the composite material by volume. Fibers can compose from 1-90% of the material by volume. DGS can compose between 2-30% of the substrate by volume. The inoculum, when in the form of grain, can compose between 1-70% of the substrate by volume. The inoculum, when in other forms can comprise up to 100% of the substrate. Ground cellulose, sourced from waste paper, can compose from 1-30% of the substrate by volume.

Other embodiments may use an entirely different set of particles from either agricultural or industrial sources in ratios sufficient to support the growing of filamentous fungi through their mass.

Though not detailed in this preferred embodiment, the engineered substrate can also contain elements and features including: rods, cubes, panels, lattices, and other elements with a minimum dimension 2 times larger than the mean diameter of the largest average particle size.

In this embodiment, the fungi strain *Pleurotus ostreatus* was grown through the substrate to produce a bonded composite. Many other filamentous fungi's could be used to produce a similar bonding result with differing final composite strength, flexibility, and water sorption characteristics.

In this embodiment, the substrate was inoculated using *Pleurotus ostreatus* growing on rye grain. Other methods of inoculation, including liquid spore inoculation, and liquid tissue inoculation, could be used with a similar result.

Incubation of the composite was performed at 100% RH humidity at 75° Fahrenheit. Successful incubation can be performed at temperatures as low as 35° Fahrenheit and as high as 130° Fahrenheit. RH humidity can also be varied to as low as 40%.

Drying was accomplished using a convection oven but other methods, including microwaving and exposing the composite to a stream of cool, dry air, are both viable approaches to moisture removal.

EXAMPLE 5

Static Embodiment—Composite with Unique Shape and Internal Features

FIG. 7 shows a perspective view of one embodiment of a mycelia bonded composite composed of nutritional particles, bulking particles, fibers, and insulating particles. This embodiment includes a void near the center that is preserved in the final composite. The preferred use for this composite is a packing material wherein the device to be packed is completely, or partially, placed within a void or series of voids formed by the grown composite.

In this embodiment of a mycelia bonded composite, the following growth conditions and materials were used: The engineered substrate was composed of the following constituents in the following percentages by dry volume:
1. Rice Hulls, purchased from Rice World in Arkansas, 50% of the substrate.
2. Horticultural Perlite, purchased from World Mineral of Santa Barbra Calif., 15% of the substrate.
3. DGS, dried distillers grains, sourced from Troy Grain Traders of Troy N.Y., 10% of the substrate.
4. Ground cellulose, composed of recycled paper ground into an average sheet size of 1 mm×1 mm, 10% of the substrate.
5. Coco coir, sourced from Mycosupply, 10% of the substrate.
6. Inoculum composed of rye grain and inoculated with *Pleurotus Ostreatus*, 3% of the substrate.
7. Birch sawdust, fine ground, 2% of the substrate by volume.
8. Tap water, from the Troy Municipal Water supply, was added until the mixture reached field capacity, an additional 30% of the total dry substrate volume was added in the form of water.

These materials were combined together in a dry mix process using a rotary mixer to fully incorporate the particles, nutrients, and fibers. Water was added in the final mixing stage. Total mixing time was 5 minutes.

After mixing, the inoculated substrate was transferred to a series of rectangular enclosures, Lids were placed on these enclosures containing block shaped extrusions. These extrusions produced corresponding net shape voids in the loose fill particles as indicated in FIG. 7.

FIG. 9 shows a growth enclosure lid with a protrusion 21. When this lid is used in conjunction with a matching bottom growth enclosure, the protrusion 21 will effect the overall net shape of the enclosed volume producing features in the grown composite that relate directly to those in the lid, such as protrusion 21. Such a process was used to produce the composite shown in FIG. 7 where the lid, shown in FIG. 9 has a protrusion 21, that modifies the enclosed net volume of its growth enclosure producing a unique feature 12 within composite 10 (see FIG. 7).

The enclosures were incubated for 14 days at 100% RH humidity and at a temperature of 75° Fahrenheit. The enclosures serve as individual microclimates for each growing substrate set. By controlling the rate of gas exchange, humidity can be varied between RH 100%, inside an enclosure, and the exterior humidity, typically RH 30-50%. Each rectangular enclosure fully contained the substrate and inoculum preventing gaseous exchange. Opening the enclosures lids after 5 and 10 days allowed gaseous exchange. In some cases, lids included filter disks allowing continuous gas exchange.

After 14 days of growth, the enclosures were removed from the incubator. The loose fill particles and fibers have now been bonded into a cohesive whole by the fungi's mycelium producing a rectangular object with a net shape closely matching that of the growth enclosure. This net shape includes a corresponding void where the enclosure lid's extrusion intersected the substrate. This panel was then removed from the enclosure by removing the lid, inverting the growth container, and pressing gently on the bottom.

The mycelia bonded panel was then transferred to a drying rack within a convection oven. Air was circulated around the panel until fully dry, about 4 hours. Air temperature was held at 130° Fahrenheit.

After drying, the now completed composite is suitable for direct application as a packaging material or can be post processed to include other features or additions including water resistant skins, stiff exterior panel faces, and paper facings.

Within the above embodiment, the ratios and percentages of bulking particles, insulating particles, fibers, nutrients, inoculum, and water can be varied to produce composites with a range of properties. The materials expanded perlite compositions can vary from 5%-95% of the composite by volume. Other particles, including exfoliated vermiculite, diatomic earth, and ground plastics, can be combined with the perlite or substituted entirely. Particle sizes, from horticultural grade perlite to filter grade perlite are all suitable for composite composition and many different composite types can be created by varying the ratio of perlite particle size or vermiculite or diatomic earth particle size.

Rice hulls can compose anywhere from 5-95% of the composite material by volume. Fibers can compose from 1-90% of the material by volume. DGS can compose between 2-30% of the substrate by volume. The inoculum, when in the form of grain, can compose between 1-30% of the substrate by volume. Ground cellulose, sourced from waste paper, can compose from 1-30% of the substrate by volume.

Other embodiments may use an entirely different set of particles from either agricultural or industrial sources in ratios sufficient to support the growing of filamentous fungi through their mass.

Though not detailed in this preferred embodiment, the engineered substrate can also contain internal elements including: rods, cubes, panels, lattices, and other elements with a dimension minima 5 times larger than the mean diameter of the largest average particle size.

In this embodiment, the fungi strain *Pleurotus ostreatus* was grown through the substrate to produce a bonded composite. Many other filamentous fungi's could be used to produce a similar bonding result with differing final composite strength, flexibility, and water sorption characteristics.

In this embodiment, the substrate was inoculated using *Pleurotus ostreatus* growing on rye grain. Other methods of inoculation, including liquid spore inoculation, and liquid tissue inoculation, could be used with a similar result.

Incubation of the composite was performed at 100% RH humidity at 75° Fahrenheit. Successful incubation can be performed at temperatures as low as 35° Fahrenheit and as high as 130° Fahrenheit. RH humidity can also be varied to as low as 40%.

In this embodiment, only one void of a square shape was shown, but such a product could include multiple voids in many shapes to match the dimensions of product enclosed within the voids.

EXAMPLE 6

Growth Enclosure—FIG. 8

Referring to FIG. 8, a square growth enclosure is provided with a lid to produce composite panels with an equivalent net shape. The panels are produced using a process similar to that outlined in example 1 and 2.

The shape of the enclosure used for composite production determines the eventual shape of the final product. In FIG. 8, the orthogonally oriented sides, left 13 and front 14, form a corner with bottom 15, this corner feature, as other enclosure induced net shapes, will be replicated in the grown composite.

Beyond producing the equivalent net shape of a grown composite, the enclosure provides a number of other unique functions. These include: gas exchange regulation, humidity regulation, humidity sensing, temperature sensing, and heat removal.

FIG. 8 shows a filter disk 16 that is sized and calibrated to the shape and volume of the growth enclosure. This filter disk 16 allows the growing organism to respirate, releasing $CO_2$ and up taking $O_2$ without the exchange of other particles in the room. This disk 16 also allows some moisture to travel from substrate to the incubation environment, and vice versa. Typically, a filter disk system would be passive, designed to allow the correct respiration rate for the specific substrate, fungi type, and volume of material, growing within the enclosure. In some cases, where active control over an individual incubation environment is desired, a filter disk could have an aperture that is dynamically altered to slow or increase the rate of gaseous exchange with the incubation environment.

FIG. 8 also shows a temperature control mechanism 17, comprised of a network of tubing 20, that can be used to remove or add heat to the enclosure. The growth of fungi relies on a decomposition reaction. Hence, in most cases where additional heat control is required beyond that provided by the convective interactions occurring along the exterior enclosures surface, it will be in the form of heat removal. A network of tubes or other heat exchange mechanism allows both more precise control over the amount of heat removed or added to the enclosure and allows an overall greater amount of heat to be removed or added to the growth enclosure in a shorter period of time.

FIG. 8 also shows a temperature sensor 18 and humidity sensor 19. These sensors measure the internal temperature and humidity of the enclosure, respectively. This data can then be transmitted to a collection unit for analysis, or be used to alter the environment of the enclosure through the dynamic re-sizing of a filter disk aperture or through changes in temperature made possible through the temperature control mechanism.

EXAMPLE 7

Figure 11:
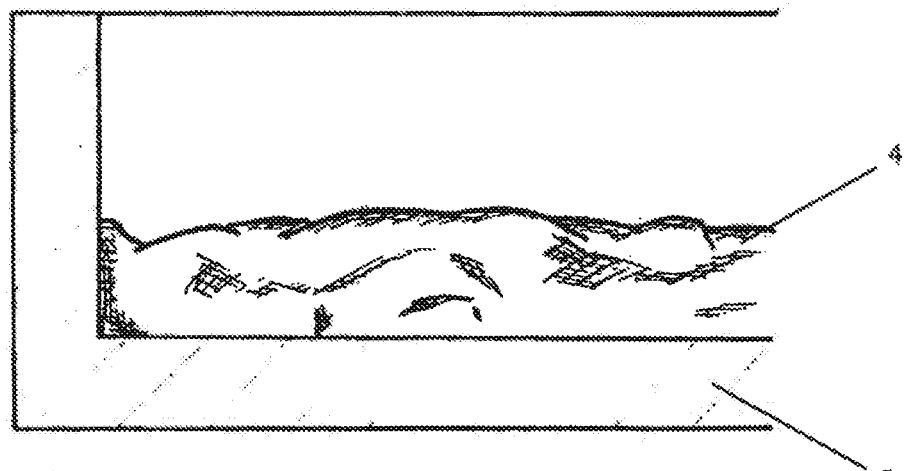
FIG. 11 illustrates a layered substrate with an added layer in accordance with the invention.
Figure 12:
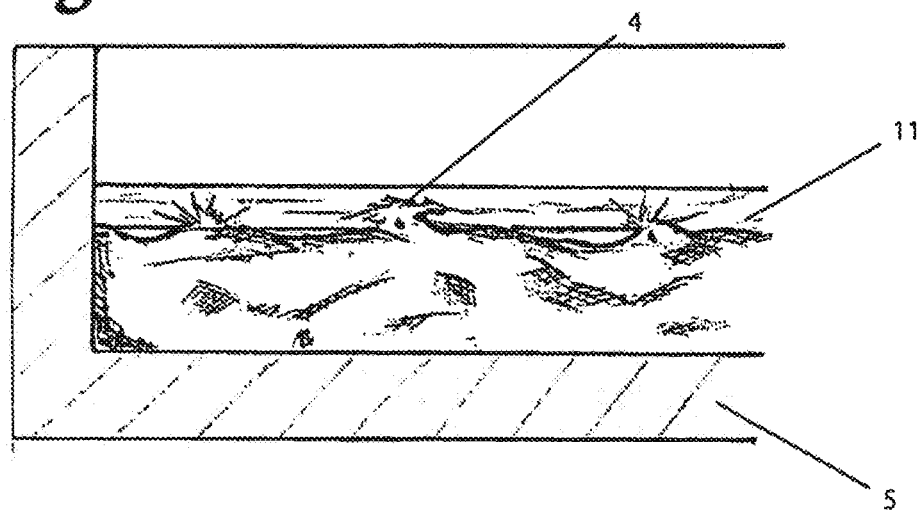
FIG. 12 illustrates hyphae growing into a layered substrate in accordance with the invention.

Growth Enclosure—FIGS. 10, 11 and 12

Growth enclosures may become part of the final product in part, or in their entirety. FIGS. 10 through 12 illustrate just such a case.

In FIG. 10, the growth enclosure 5 and growing mycelium 4 are bounded only by the bottom and sides of the growth enclosure.

In FIG. 11, a stiff sheet 11 comprised of OSB (oriented strand board) or other suitable veneer is added to the enclosure 5, fully defining the volume of the growth enclosure. In this case, the enclosure cover was selected from a group comprising wood, and other cellulosic structures. As such, the fungi, *Pleurotus ostreatus*, a cellulosic decomposer, being grown through the enclosure, was able to naturally bond itself to the top portion of the panel by growing along and into the surface of the material.

FIG. 12 illustrates the growth of mycelia 4 into the stiff sheet 11. When this composite is removed from the enclosure, the stiff sheet 11 will be included in the final product.

FIG. 12 illustrates an alternative embodiment of this same concept wherein the stiff sheet 11 is enclosed between two opposing layers of mycelia bonded core.

Growth enclosures comprised entirely or in part of stiff or flexible sheets 11 may be permanently attached to part, or all, of the finished product through the growth of mycelium. This includes bags that hold a form, bags that are flexible and can be formed into shapes within an enclosure, and other means for containing a slurry.

Another example where such a process might occur uses a flexible paper bag as the growth enclosure. This bag is filled with engineered substrate and the mycelium is grown through the substrate as described in Example 1. Bonding of the substrate to the bag occurs through the growth of the mycelium and, when dried, a product comprising a bonded engineered substrate and exterior paper skin is produced The above methods of bonding assume that cellular interactions due to the cellulosic decomposition of the substrate enclosure are the primary method of bonding but this need not be the only case of mycelia and partial enclosure adhesion (enclosure in this case is meant to comprise any stiff or flexible material in contact with an engineered substrate during growth).

Other methods of bonding include 'roughening' the surface of the object to bond or adding protrusions to the surface of said object. These protrusions may be only a fraction of a millimeter tall (in the case of roughening) or may be up to 20 cm tall, extending into the engineered substrate. Protrusions may take the form of: hooks, circular poles, cones, rectangular columns, capped columns or poles, triangles, or other feature shapes that allow mycelia to favorably interact with the surface to produce a bonding force.

EXAMPLE 8

An Acoustic Dampening Panel

In accordance with the procedure outlined in Examples 1 and 2 and the particle and growth conditions outlined in Example 4, an acoustical dampening panel could be produced for use within the home, automobile, or other situation where sound attenuation is desired. This product would use a variety of bonded fibers and particles to produce panels with varying sound attenuation rates for a set range of frequencies.

EXAMPLE 9

A Rigid Firewall

In accordance with the procedure outlined in Examples 1 and 2 and the particle and growth conditions outlined in Example 4, a firewall panel could be produced for use within the home, automobile, or other situation where fire protection is desired. In this panel the bonded particles would be composed primarily of Perlite, Rice Hulls, or Vermiculite.

EXAMPLE 10

Production Using Feature Molding

Production of a grown material using an enclosure and feature molding, i.e. a tool or other object to create a feature relief within a growing shape of substrate.

*Plearotus Ostreatus*, or any other filamentous fungi, is cultured from an existing tissue line to produce a suitable mass of inoculum. The inoculum may take the form of a solid carrier, liquid carrier, or any other variation there of.

To produce a grown material using a molding based manufacturing technique, the following steps are taken:
1. Creation of an engineered substrate comprised of nutritional particles, fibers, non-nutritional particles, and other elements.
2. Disposition of the substrate within an enclosure or series of enclosures with voids designed to produce the desired final shape.
3. Inoculation of the substrate within the enclosure with the inoculum containing the desired fungi strain.
4. Growing the desired fungi strain through the engineered substrate within the enclosure or enclosures.
5. Forcefully molding additional features into the engineered substrate by compressing a tooling piece with extruded features into one of the faces of the engineered substrate.
6. Allowing the living substrate to recover.
7. Removal of the substrate from the enclosure or enclosures.

Alternatively, the method may use the following steps:
1. Creation of an engineered substrate comprised of nutritional particles, fibers, non-nutritional particles, and other elements.
2. Inoculation of the engineered substrate with the inoculum containing the desired fungi strain.
3. Disposition of the substrate within an enclosure or series of enclosures with voids designed to produce the desired final shape.
4. Growing the desired fungi strain through the engineered substrate within the enclosure or enclosures.
5. Forcefully molding additional features into the engineered substrate by compressing a tooling piece with extruded features into one of the faces of the engineered substrate.
6. Allowing the living substrate to recover.
7. Removal of the bonded engineered substrate from the enclosure or enclosures.

EXAMPLE 11

Figure 13:
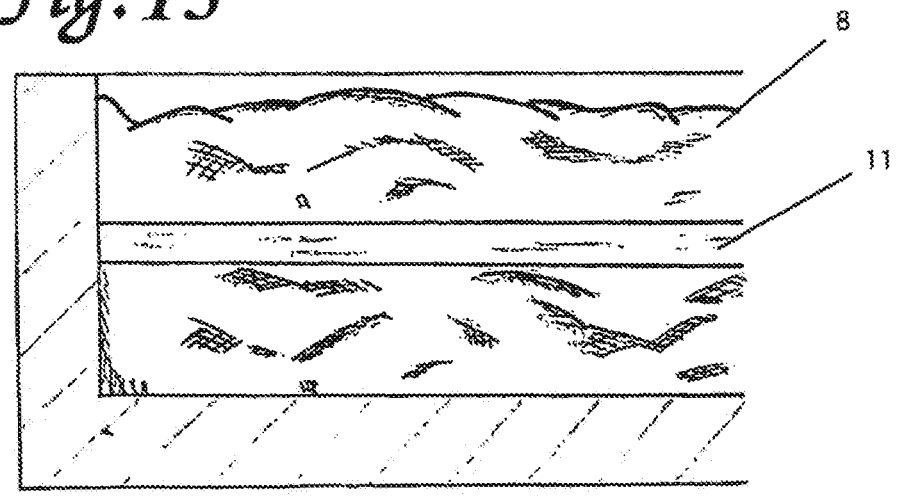
FIG. 13 illustrates a packaging egg in accordance with the invention

Packaging Egg—FIG. 13

Using the manufacturing process described in Examples 1 and 2, a distinctly unique packaging material can be created that makes use of the mycelium bonders ability to form a continuous material. By placing a three dimensional object to be packaged in a enclosure and then surrounding the object with an engineered substrate, bound by mycelium, a packaging material can be created that exactly fits every surface of the packaged object. This packaging material is continuous around the packaged object, and because of its tight fit will better protect a packed object than the current state of the art that uses "near net shape" packing buffers to hold objects in place.

Such a product is detailed in FIG. 13 wherein a continuous packaging material was formed around an object 23 to form a package.

The packaging material is characterized in being rupturable into discrete sections along a break surface 25, as shown in FIG. 13 to allow removal of the sections from the object 23. Alternatively, a ribbon 24 can be wrapped about the object 23 to extend through the packaging material to an external surface of the packaging material for rupturing the packaging material into discrete sections for removal from the object 23.

Upon receipt of the packing egg, the end user opens the packaging egg either by breaking the material along one of its axis, or pulling on an included ribbon 24, as shown, or a string or tab. Once opened, the user can then remove the protected object 23.

A packaging egg can be made using the same substrate and processes described in example 4 and examples 1 and 2 respectively. Substrate particle and fiber choice will be governed by the overall material characteristics of the egg. A denser packaging material will necessitate denser bulking particles, while a lighter more compressible egg would rely on lighter particles, such a rice hulls.

Briefly, the following steps can be undertaken to produce a packaging egg: To produce a grown packaging egg using an enclosure based manufacturing technique, the following steps are taken:
1. Creation of an engineered substrate comprised of nutritional particles, fibers, non-nutritional particles, and other elements.
2. Disposition of the substrate within an enclosure or series of enclosures with voids designed to produce the desired final shape.
3. Disposition of the product to be packaged within the loose substrate.
4. Inoculation of the substrate within the enclosure with the inoculum containing the desired fungi strain.
5. Growing the desired fungi strain through the engineered substrate within the enclosure or enclosures and around the material to be packaged,
6. Removal of the substrate from the enclosure or enclosures.

Alternatively, the method may use the following steps:
1. Creation of an engineered substrate comprised of nutritional particles, fibers, non-nutritional particles, and other elements.
2. Inoculation of the engineered substrate with the inoculum containing the desired fungi strain.
3. Disposition of the substrate within an enclosure or series of enclosures with voids designed to produce the desired final shape.
4. Disposition of the product to be packaged within the loose substrate
4. Growing the desired fungi strain through the engineered substrate within the enclosure or enclosures and around the afore mentioned packaged material.
5. Removal of the bonded engineered substrate from the enclosure or enclosures.

Alternatively, the product to be packaged may be placed in the enclosure before the addition of the substrate, during the addition of the substrate, or after addition of the substrate.

Growth, substrate type, fungi strain, and incubation details are similar to those outlined in EXAMPLE 4 though all of these variables can be modified to produce packaging eggs with different material properties and behavior Briefly, a packaging egg is composed of a fully internal or partially internal element surrounded by a continuous skin or material wall. This wall is preferably composed of a particles, fibers, and other elements bound by mycelium that has been grown through the elements.

The packaging egg, as described, has a number of unique advantages. First, the material is biodegradable, so the user can dispose of the material into their garden, or other natural space, after use, reducing landfill load. Second, the continuous nature of the grown packaging material provides both better protection during shipment and acts as a tamper proof seal preventing unauthorized access to the packaged element. Third, the packaging egg can be produced with minimal tooling costs as the formable substrate will assume the net shape of both enclosure and packaged element.

EXAMPLE 12

Figure 14:
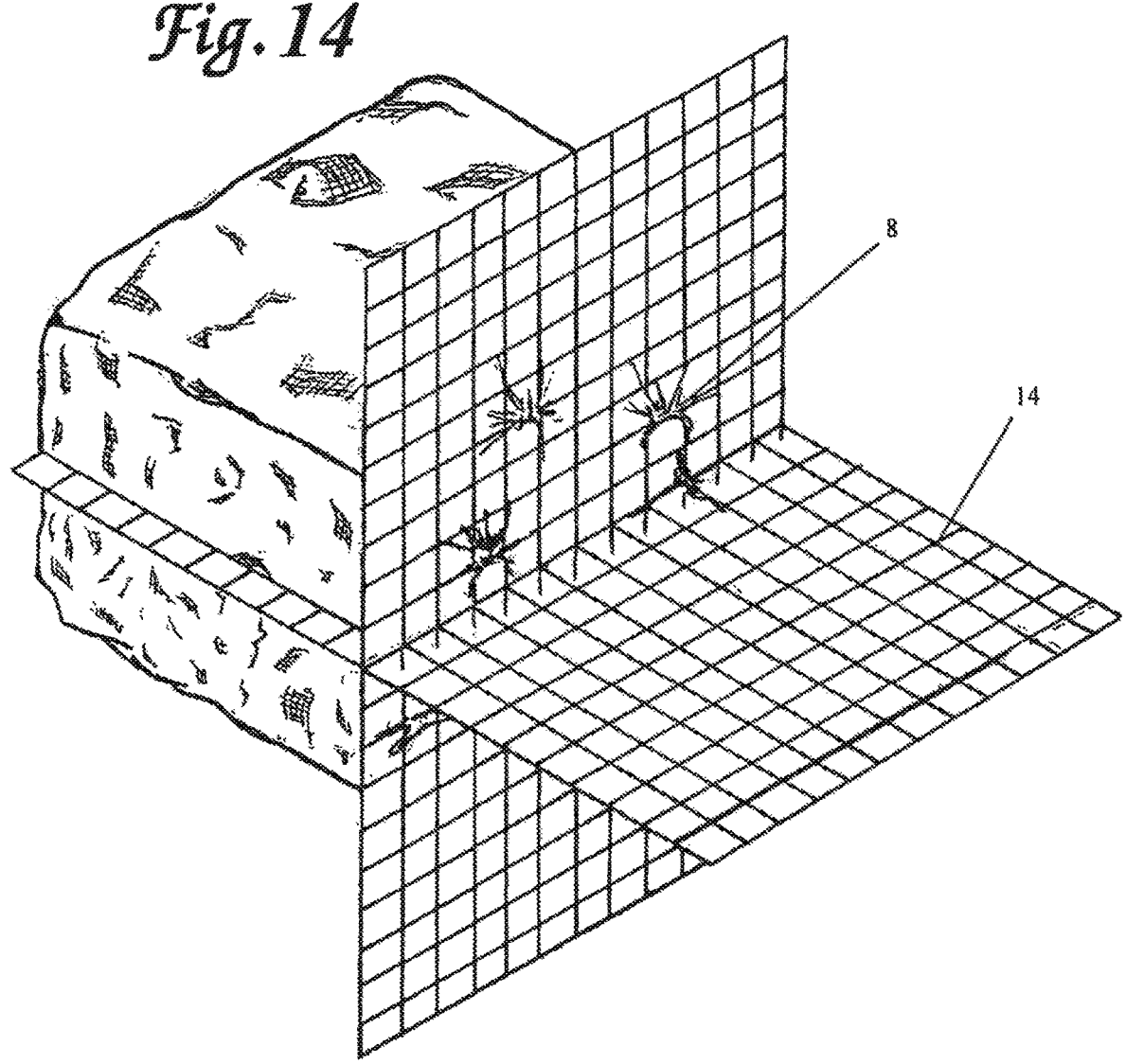
FIG. 14 illustrates a section of a wall board made in accordance with the invention.
Figure 15:
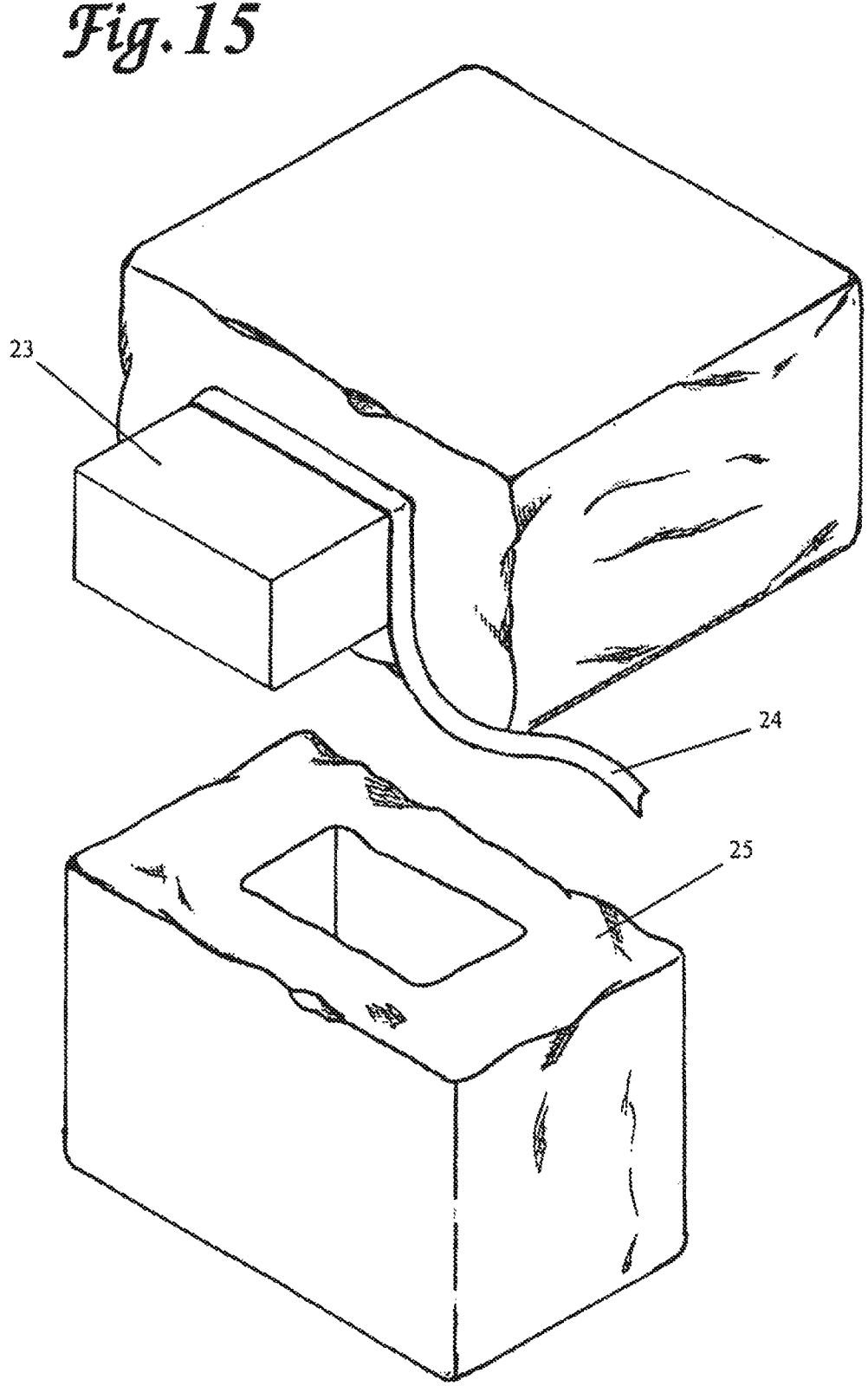
Figure 16:
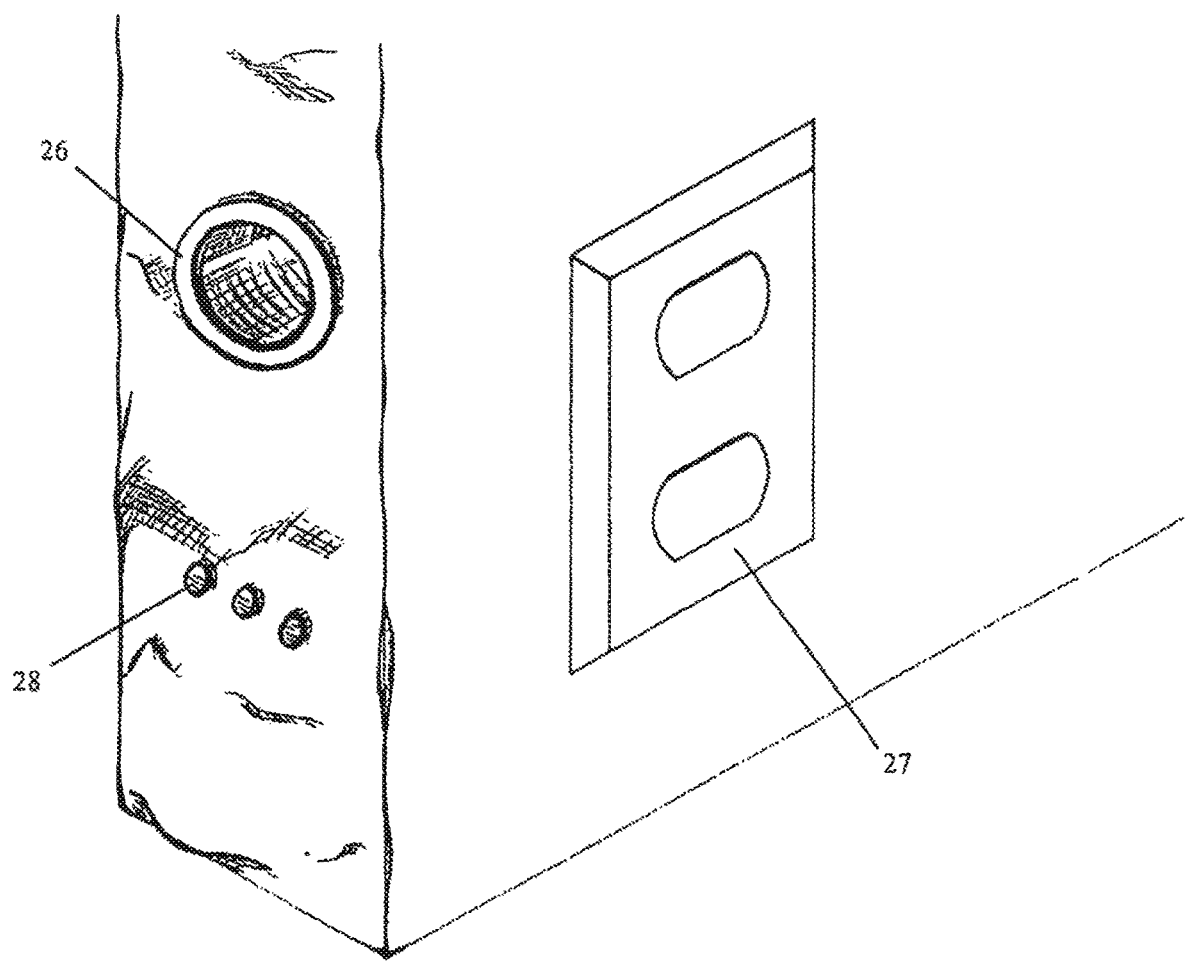

Wall Panel with Molded Features—FIG. 14

FIG. 14 shows a composite panel, produced in accordance with the production processes described in Examples 1, 2, & 3, with a static embodiment and composition similar to that described in Example 4.

The panel that also includes a number of wall elements, such as a conduit 26, an electrical outlet 27 and wires 28, that are embedded in the composite material of the panel and have an end in communication with an exterior surface of the composite material. These elements are included within the panel during the growth processes in such a manner that they become part of the final monolithic composition. These elements may be selected from the groups comprising: generic conduit, electrical wiring, electrical outlets, light switches, sensors, temperature controls, window frames, door jams, heating conduit, or piping.

Additionally, such elements may be positioned within the panel such that when panels are placed edge to edge the internal elements interface along the mating edge.

Such a panel could be produced and sold as is, without additional processing, or could be combined with the stiff exterior faces to produce a full section for use in assembling a home. Such a wall section could have all relevant elements included during growth such that final assembly would constitute only connecting matching panels and internal elements together.

Alternative Substrates

Organic materials can be implemented in the mycelium insulation growth process as insulating particles and the complex carbohydrate. Currently, insulating particles such as vermiculite or perlite are bound within the mycelium cellular matrix, but other natural materials have identical if not superior insulating characteristics, such as:

Straw/Hay/Hemp: material is either woven into a mesh or laid within the slurry mixture, as the mycelium grows the material is bound forming an insulation panel with variable layer thickness.

Wool/Cotton: the material is woven into a fibrous mesh or fragmented forming small insulating particles that a bound within the mycelium as it grows. The slurry can be applied directly to the mesh or the particles can be mixed in during the slurry production. The particle material can be grown or obtained from reused clothing that contains a large percentage of wool/cotton.

Recycled sawdust can replace the current polysaccharide, which is a form of starch or grain, as the mycelium food source during the early growth stages. Sawdust can be collected from businesses that create the dust as a byproduct or from natural collections methods.

The insulating particles can consist of new, recycled, or reused synthetic particles, which are already known to have insulating properties or leave a detrimental environmental footprint. Materials currently considered include:

Foam Based Products: recycled and reused foam insulators or foam garbage, such as Styrofoam cup and packaging, which are broken into small particles of varying or congruent sizes and applied to the slurry. The foam material can be obtained from existing disposed of material or newly fabricated products.

Rubber/Polymers: these materials can be found in a myriad of products, which can be reused after the desired life-cycle of the aforementioned product is reached. The material can be applied into the slurry as a ground particle or implemented as a structural member within the growth in various configurations.

The invention thus provides a new method of producing grown materials. These materials may be flexible, rigid, structural, biodegradable, insulating, shock absorbent, hydrophobic, hydrophilic, non-flammable, an air barrier, breathable, acoustically absorbent and the like. All of the embodiments of this invention can have their material characteristics modified by varying the organism strain, nutrient source, and other particles, fibers, elements, or other items, included in the growth process.

Further, the invention provides a composite material that can be used for various purposes, such as, for construction panels, wall boards, and the like where fire-resistant characteristics are required. Also, the invention provides a composite material that is biodegradable.

The preferred method described above for killing the growing organism, i.e. a fungi, in order to stop further growth is by heating to above 110 degrees Fahrenheit, there are a number of other ways that this same task can be accomplished. These include (a) dehydrating—by placing the mycelium bonded substrate in a low humidity environment; (b) irradiating—by using a technique similar to that found in food preservation; (c) freezing—wherein the mycelium bonded substrate has its temperature lowered to below 32 degrees Fahrenheit; and (d) chemically—wherein the mycelium bonded substrate is exposed to a chemical known to cause cellular death in fungi including, but not limited to, bleach solutions, high concentrations of petrochemicals, and high concentrations of acids.

What is claimed is:

1. A self-supporting composite material comprising
a substrate of discrete particles; and
a network of interconnected mycelia cells extending through and around all of said discrete particles to fully colonize said substrate and bond said discrete particles together.

2. A self-supporting composite material as set forth in claim 1 wherein said particles are selected from the group consisting of at least one of vermiculite and perlite.

3. A self-supporting composite material as set forth in claim 1 wherein said particles are selected from the group consisting of at least one of straw, hay, hemp, wool, cotton and recycled sawdust.

4. A self-supporting composite material as set forth in claim 1 wherein said particles include synthetic insulating particles.

5. A self-supporting composite material as set forth in claim 4 wherein said synthetic insulating particles include foam based products and polymers.

6. A self-supporting composite material as set forth in claim 1 wherein said particles are in the form of fibers.

7. A self-supporting composite material as set forth in claim 1 further comprising elements in said substrate having a dimension 5 times larger than the mean diameter of the largest average particle size.

8. A self-supporting composite material as set forth in claim 7 wherein said elements are at least one of rods, cubes, panels, and lattices.

9. A self-supporting composite material as set forth in claim 7 wherein said elements are selected from the group including conduit, electrical wiring, electrical outlets, light switches, sensors, temperature controls, window frames, door jambs, and piping.

10. A self-supporting composite material as set forth in claim 1 further comprising at least one mechanical element at least partially embedded in said substrate and having a dimension 5 times larger than the mean diameter of the largest average particle size.

11. A self-supporting composite material as set forth in claim 10 wherein said element is selected from the group including conduits, electrical wiring and electrical outlets.

12. A self-supporting composite material as set forth in claim 1 further comprising a stiff sheet of material bonded thereto.

13. A self-supporting composite material as set forth in claim 1 characterized in having a rectangular panel shape and further comprising a stiff sheet of material bonded to at least one side thereof.

14. A self-supporting composite material as set forth in claim 1 characterized in being a thin flexible mat.

15. A self-supporting composite material as set forth in claim 1 characterized
in being a fire wall wherein said discrete particles include perlite, rice hulls and vermiculite.

16. A self-supporting composite material comprising
a substrate of discrete bulking particles; and
a network of interconnected mycelia cells extending through and around all of said discrete particles to fully colonize said substrate and bond said discrete bulking particles together.

17. A self-supporting composite material as set forth in claim 16 wherein said particles are in the form of fibers.

18. A self-supporting composite material as set forth in claim 16 characterized in having a rectangular panel shape and further comprising a stiff sheet of material bonded to at least one side thereof.

* * * * *